United States Patent [19]

Saita et al.

[11] Patent Number: 5,175,286

[45] Date of Patent: Dec. 29, 1992

[54] DIBENZ[B,E]OXEPIN DERIVATIVES

[75] Inventors: Masaru Saita, Miyaki; Hisataka Inoue, Kurume; Terumi Hachiya, Kanzaki; Mikio Nakashima, Tosu; Shigenori Yahiro, Kasuya; Yasuaki Taniguchi, Tosu; Yoshiki Deguchi, Tosu; Shoji Hamanaka, Tosu; Masayoshi Tsuji, Tosu; Kanji Noda, Chikushino, all of Japan

[73] Assignee: Hisamitsu Pharmaceutical Co., Inc., Tosu, Japan

[21] Appl. No.: 651,389

[22] PCT Filed: Sep. 12, 1989

[86] PCT No.: PCT/JP89/00932

§ 371 Date: Mar. 8, 1991

§ 102(e) Date: Mar. 8, 1991

[87] PCT Pub. No.: WO90/03373

PCT Pub. Date: Apr. 5, 1990

[30] Foreign Application Priority Data

Sep. 20, 1988 [JP] Japan .................. 63-23780

[51] Int. Cl.$^5$ ......................................... C07D 413/12
[52] U.S. Cl. ..................................... 544/147; 544/375; 546/196; 548/525; 549/354
[58] Field of Search ............... 549/354; 544/147, 375; 546/196; 548/525

[56] References Cited

U.S. PATENT DOCUMENTS

| 4,228,284 | 10/1980 | Yamabe et al. | 544/375 |
| 4,255,431 | 3/1981 | Jauggren et al. | 424/263 |
| 4,282,365 | 8/1981 | Rokach et al. | 549/354 |
| 4,359,465 | 11/1982 | Ruwart | 424/263 |
| 4,599,347 | 7/1986 | Krässó et al. | 514/338 |

FOREIGN PATENT DOCUMENTS

| 0176308 | 4/1986 | European Pat. Off. | 548/305 |
| 0124495 | 1/1987 | European Pat. Off. | 546/271 |
| 0208452 | 1/1987 | European Pat. Off. | 514/338 |
| 0221041 | 5/1987 | European Pat. Off. | 546/271 |
| 0279149 | 11/1987 | European Pat. Off. | 514/338 |
| 1500043 | 2/1978 | United Kingdom | 548/305 |
| 1525958 | 9/1978 | United Kingdom | 514/338 |
| 2134523 | 8/1984 | United Kingdom | 546/271 |

Primary Examiner—C. Warren Ivy
Assistant Examiner—Raymond Covington
Attorney, Agent, or Firm—Bucknam and Archer

[57] ABSTRACT

A dibenz[b,e]oxepin derivative represented by the formula (I)

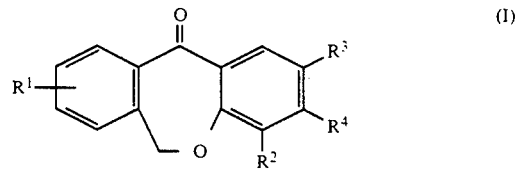

wherein $R^1$ and $R^2$ are each hydrogen, halogen, lower alkyl or alkoxy; one of $R^3$ and $R^4$ is lower alkoxy, and other is a group represented by the formula (II)

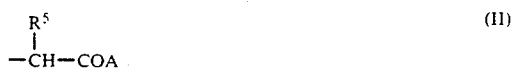

wherein $R^5$ is hydrogen or lower alkyl, A is hydroxyl, $-O(CH_2)_m-R^6$ (wherein m is an integer of 1-6, $R^6$ is hydrogen, lower alkyl or alkoxy, cycloamino, or lower alkoxycarbonyl), cycloamino, di-lower alkylamino or $-NH(CH_2)_n-R^7$ (wherein n is an integer of 0-3, $R^7$ is hydrogen, hydroxyl, phenyl, thiazole or cycloamino).

8 Claims, No Drawings

DIBENZ[B,E]OXEPIN DERIVATIVESDESCRIPTION

1. Technical Field

The present invention relates to a novel dibenz[b,e] oxepin derivative which is a non-steroid type antiphlogistic agent having anti-inflammatory, analgesic actions, extremely slight gastroenteric troubles and particularly high safety.

2. Background Art

Compounds having a dibenz[b,e]oxepin nucleus to the 2-position or 3-position of which is attached an alkanic acid such as acetic acid or propionic acid, have been reported in Japanese Pat. Appln. Laid-Open Gazettes Nos. 50-35179 and 50-58084, Japanese Pat. Gazette No. 55-32708, "Journal of Medicinal Chem., Vol. 19, No. 7, pp. 941-946 (1976)", and "Arch. int. Pharmacodyn, 227, pp. 142-154 (1977). Some of these publications indicate that said compounds have anti inflammatory, analgesic actions. The above publications neither disclose nor even suggest anything about dibenz[b,e] oxepin derivatives not only having an alkanic acid such as acetic or propionic acid at one of the 2-position and 3 position thereof but also having a lower alkoxy group at the other as in the compounds of the present invention.

Conventional non-steroid type acidic antiphlogistics typified by indomethacin, aspirin and the like, as compared with basic antiphlogistics, will exhibit clear pharmacological actions whereas they will have unfavorable side effects on digestive tracts such as stomachs and intestines when administered to life. Gastric ulcers and duodenal ulcers will frequently occur as said side effects whereby said conventional acidic antiphlogistics are limited in use as a medicine.

Thus, in an attempt to provide compounds which have solved the above problems, many compounds have been synthenized. The compounds so synthesized, however, are not appreciated to be satisfactory ones. For example, the compounds described in said Japanese Pat. Appln. Laid-Open Gazette No. 50-35179 and "Journal of Medicinal Chem., vol. 19, No. 7, pp.941-946 (1976)" are now devalued as a medicine since they tend to cause gastroenteric tract troubles as in the above-mentioned antiphlogistics.

The primary object of the present invention is to provide novel compounds which, when administered, will not only exhibit excellent analgesic and anti-inflammatory effects but also have remarkably low side effects (the side effects being such as gastroenteric tract troubles) and toxicity with high safety, as compared with conventional anti-inflammatory, analgesic agents.

SUMMARY OF THE INVENTION

The present inventors made various intensive studies in view of the above problems and, as the result of their studies, found that said problems are solved by the following compounds. The present invention is based on this finding or discovery.

The compounds of the present invention are dibenz[b,e]oxepin derivatives represented by the following formula (I)

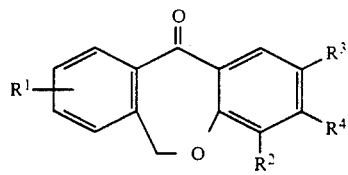

wherein $R^1$ and $R^2$ are each a hydrogen atom, halogen atom, lower alkyl group or lower alkoxy group; one of $R^3$ and $R^4$ is a lower alkoxy group, and the other is a group represented by the following formula (II)

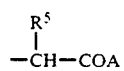

wherein $R^5$ is a hydrogen atom or lower alkyl group, A is a hydroxyl group, $-O(CH_2)_m-R^6$ (wherein m is an integer of 1-6, $H^6$ is a hydrogen atom, lower alkyl group, lower alkoxy group, piperazino, morpholino, piperidino group, pyrrolidino group or lower alkoxycarbonyl group, di-lower alkylamino group or $-NH(CH_2)_n-R^7$ (wherein n is an integer of 1-3, $R^7$ is a hydrogen atom, hydroxyl group, phenyl group, thiazole group or piperazino, morpholino, piperidino or pyrrolidino group.

The compounds of the present invention will be explained in further detail hereunder.

Firstly, the substituents in the formula (I) will be further detailed below.

The $R^1$ and $R^2$ in the formula (I) are each a hydrogen atom; a halogen atom such as fluorine, chlorine, bromine or iodine; a lower alkyl group such as methyl, ethyl, n-propyl, iso-propyl, n-butyl, iso-butyl or tert.-butyl; or a lower alkoxy group such as methoxy, ethoxy, n propoxy, iso-propoxy, n-butoxy, iso-butoxy, or tert.-butoxy.

As previously mentioned, one of $R^3$ and $R^4$ in the formula (I) is a lower alkoxy group, and the other is a group represented by the following formula (II)

The $R^5$ in the above formula (II) is a hydrogen atom, or a lower alkyl group such as methyl, ethyl, n-propyl, isopropyl, n-butyl or iso-butyl.

The symbol "A" in the above formula (II) is any one of the following groups (a)—(1):

(a) a hydroxyl group,
(b) a lower alkoxy group (having preferably 1–6 carbon atoms),
(c) a group represented by the following formula

wherein m1 is an integer of 1–6, preferably 1–3, and $R^8$ is a lower alkyl group having 1–6 carbon atoms,
(d) a group represented by the following formula

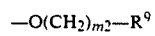

wherein m2 is an integer of 1–6, and $R^9$ is a pyrrolidino group, piperidino group, morpholino group or piperazino group,
(e) a group represented by the following formula —O(CH$_2$)$_{m3}$COOR$^{10}$ wherein m3 is an integer of 1-6, preferably 1-3, and R$^{10}$ is a lower alkyl group having 1-6 carbon atoms,
(f) a group containing 5 to 6-membered ring (the group being preferably a pyrrolidino group, piperidino group, morpholino group or piperazino group),
(g) a di-lower alkylamino group (having preferably 1-4 carbon atoms in the lower alkyl group),
(h) a group represented by the following formula —NH(CH$_2$)$_{n1}$—H wherein n1 is an integer of 0-3,
(i) a group represented by the following formula —NH(CH$_2$)$_{n2}$—OH wherein n2 is an integer of 0-3,
(j) a group represented by the following formula

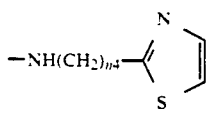

wherein n3 is an integer of 0-3,
(k) a group represented by the following formula

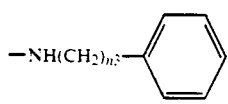

wherein n4 is an integer of 0-3, and
(l) a group represented by the following formula —NH(CH$_2$)$_{n5}$—R$^{11}$ wherein n5 is an integer of 0-3, preferably 1-3, and R$^{11}$ is a group containing a 5 to 6-membered ring, the group being preferably a pyrrolidino group, piperidino group, morpholino group or piperazino group.

Further, the lower alkoxy group which is one of the R$^3$ and R$^4$ in the above formula (I) has preferably 1-4 carbon atoms and is exemplified by a methoxy group, ethoxy group, n-propoxy group, iso-propoxy group, n-butoxy group, iso-butoxy group or tert.-butoxy group.

If necessary, the foregoing compounds of the present invention may be reacted with an inorganic salt (such as a sodium salt, potassium salt, calcium salt, aluminum salt or hydrochloride salt or with an organic salt (such as a fumarate, maleate, succinate, phthalate, lysine, ethanolamine or pyridine salt) to produce an addition salt. Further, they may be incorporated with cyclodextrin or the like to produce an inclusion compound in order to improve themselves in stability, solubility and the like.

Further the compounds of the present invention may be incorporated with a conventional vehicle to be shaped into pharmaceutically acceptable medicinal forms. They may be in the form of tablets granules, syrups, capsules or the like for use as an oral medicine or in the form of an injection, suppository, ointment, gel, cream, lotion, liniment, plaster or the like for use as a non-oral medicine.

Methods 1-4 for preparing the compounds of the present invention will then be explained hereunder.

PREPARATION 1

The sequence of reactions for preparing a desired compound is as follows:

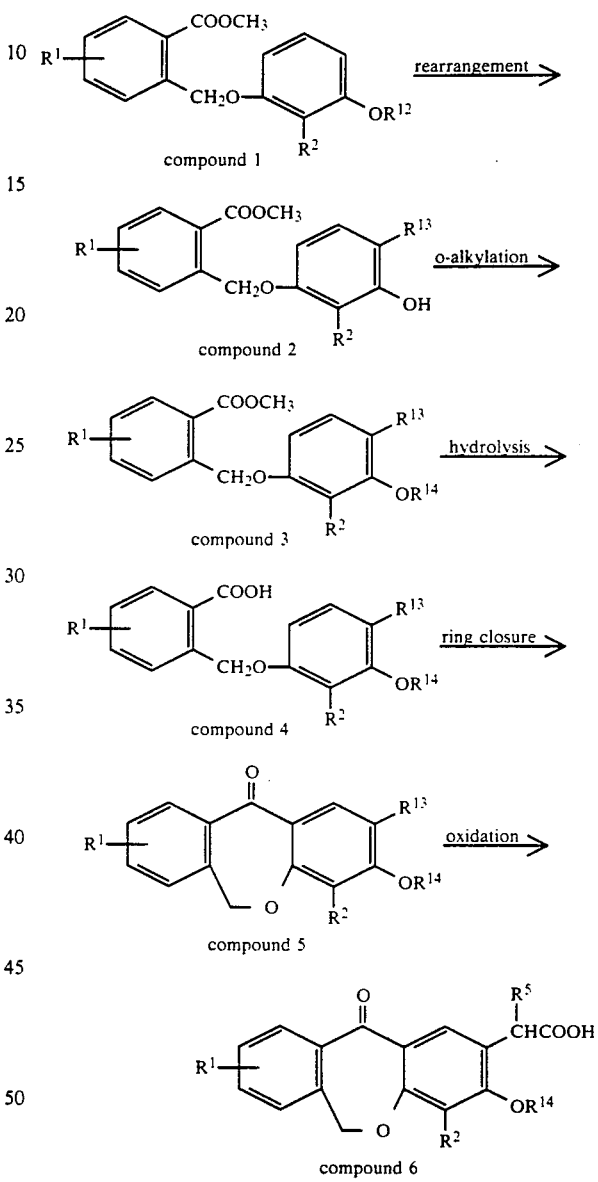

In the above formulae, R$^1$, R$^2$ and R$^5$ are each as defined above, that is, R$^1$ and R$^2$ are each a hydrogen atom, halogen atom, lower alkyl group or lower alkoxy group, and R$^5$ is a hydrogen atom or lower alkyl group; R$^{12}$ and R$^{13}$ are each an alkenyl group; and R$^{14}$ is a lower alkyl group.

Compound 1 is heated for the rearrangement thereof, o-alkylated, hydrolyzed, subjected to ring closure with anhydrous trifluoroacetic acid, polyphosphoric acid or the like and then oxidized with an oxidizer such as potassium permanganate, ozone or potassium bichromate thereby to obtain compound 6 which is a dibenz[b,e]oxepin derivative of the present invention, in a good yield.

PREPARATION 2

The sequence of reactions for preparing another desired compound is as follows:

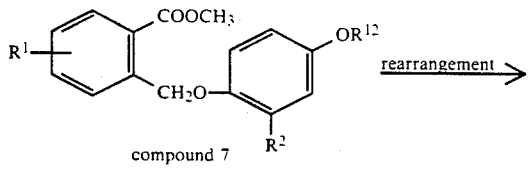
compound 7 rearrangement →

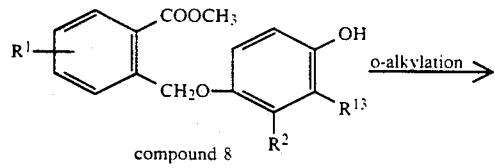
compound 8 o-alkylation →

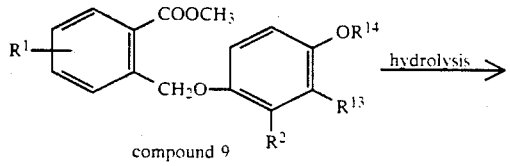
compound 9 hydrolysis →

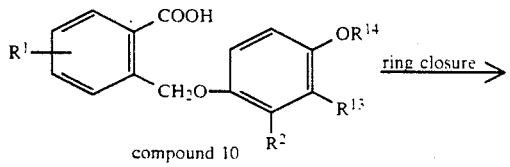
compound 10 ring closure →

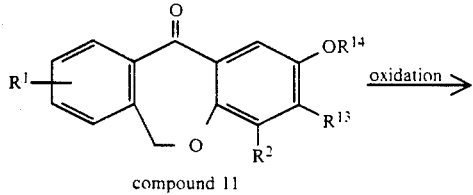
compound 11 oxidation →

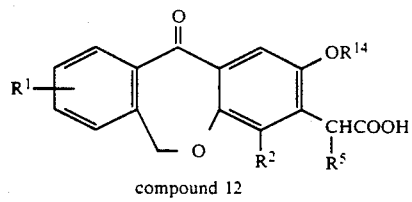
compound 12

In the above formulae, $R^1$, $R^2$, $R^5$, $R^{12}$, $R^{13}$ and $R^{14}$ are each as defined above.

Compound 7 is reacted in accordance with the foregoing Preparation 1 thereby to obtain compound 12 which is a compound of the present invention, in a good yield.

PREPARATION 3

The sequence of reactions for preparing another desired compound is as follows:

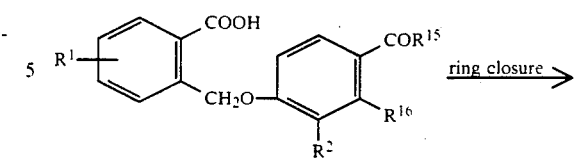
compound 13 ring closure →

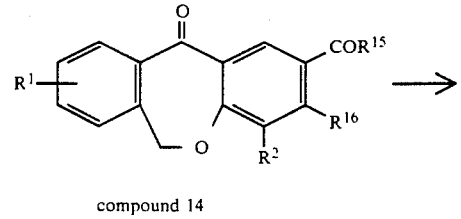
compound 14

→

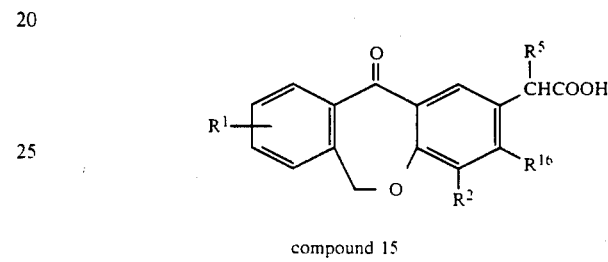
compound 15

In the above formulae, $R^1$, $R^2$ and $R^5$ are each as defined above, $R^{15}$ is a lower alkyl group and $R^{16}$ is a lower alkoxy group.

Compound 13 is subjected to ring closure and then hydrolyzed with thallium trinitrate in the presence of an acid catalyst in an alcholic solvnet, or compound 13 is subjected to ring closure and then subjected to a Willgerodt reaction, thereby to easily obtain compound 15 which is a compound of the present invention, in a good yield.

PREPARATION 4

Two kinds of reactions for preparing other desired compound are as follows:

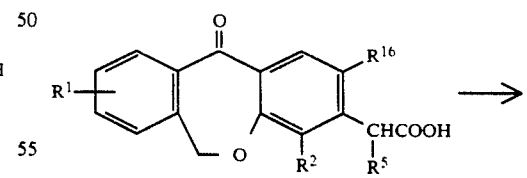
compound 16

→

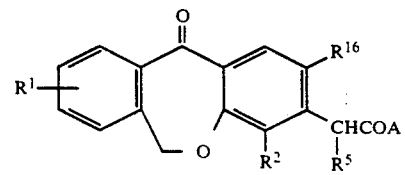
compound 17

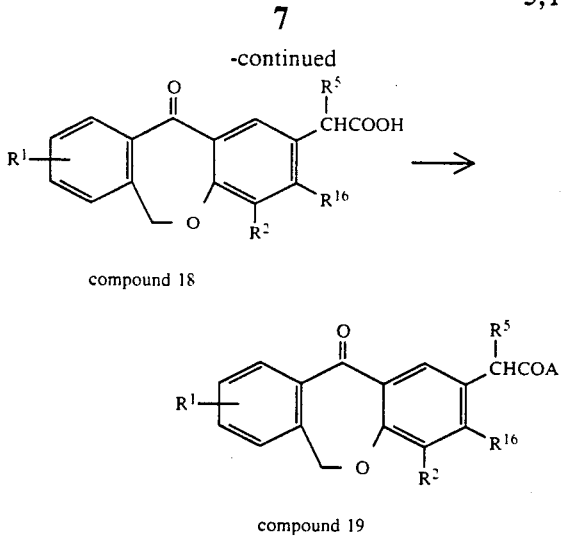

compound 18 compound 19

In the above formulae, $R^1$, $R^2$, $R^5$ and $R^{16}$ are each as defined above and A is also as defined above, that is, A is an ester residue or amino residue.

Compounds 16 and 18 are each esterified or aminated by a conventional known method thereby to obtain compounds 17 and 19 (an ester or amide) respectively, which are compounds of the present invention.

BEST MODE FOR CARRYING OUT THE INVENTION

The present invention will be better understood by the following Reference Example and non-limitative Examples.

REFERENCE EXAMPLE 13.8 g of potassium carbonate were added to 200 ml of acetone containing 22.9 g of methyl 2-bromo methylbenzoate and 38.5 g of hydroquinone, after which the whole was refluxed under agitation for 12 hours. After the end of the reaction, the reaction mixture was filtered to remove the insoluble materials therefrom and the filtrate obtained was evaporated to dryness under a reduced pressure. The residue obtained was incorporated with water to precipitate crystals which were then filtered off, after which the crystals were washed with petroleum ether to obtain 23 g of crystals of the following compound 22.

The crystals obtained were dissolved in 150 ml of acetone, incorporated with 12.9 g of allyl bromide and 7.4 g of potassium carbonate and then refluxed under agitation for 18 hours. After the end of the reaction, the insoluble materials in the reaction mixture were filtered out and the filtrate obtained was evaporated to dryness under a reduced pressure.

The residue obtained was dissolved in 40 ml of diethylaniline and reacted with each other at a temperature of 250°–270° C. for 3 hours. After cooled, the reaction mixture obtained was dissolved in 250 ml of ethyl acetate, washed with a 7% hydrochloric acid and then with water, dehydrated and then evaporated to dryness under a reduced pressure, thereby to obtain 25 g of a rearranged compound which is the following compound 24.

Further, 25 g of the rearranged compound were dissolved in 150 ml of acetone and incorporated with 6.3 g of dimethylsulfuric acid and 6.9 g of potassium carbonate, after which the whole was refluxed under agitation for 12 hours. After the end of the reaction, the insoluble materials in the reaction mixture were filtered out and the filtrate obtained was evapo-rated to dryness under a reduced pressure. The residue obtained was dissolved in 150 ml of methanol, incorporated with 25 ml of an aqueous solution of 5.0 g of sodium hydroxide and reacted together at 50° C. for 5 hours. After the end of the reaction, the reaction mixture obtained was evaporated to dryness under a reduced pressure, after which the residue obtained was incorporated with 150 ml of water and then acidified with 10% hydrochloric acid to precipitate crystals which were filtered off and dried thereby to obtain 23 g of a carboxylic acid which is the following compound 26.

Subsequently, 23 g of the carboxylic acid so obtained were dissolved in 150 m( of dichloromethane, incorporated with 48.6 g of trifluoroacetic anhydride and then reacted together under reflux for 5 hours. After the end of the reaction, the reaction mixture obtained was evaporated to dryness under a reduced pressure, after which the residue obtained was dissolved in ethyl acetate, washed with a 5% aqueous solution of potassium carbonate and then with water, dehydrated and evaporated to dryness thereby to obtain 19.5 g of 3-allyl-2-methoxy-6,11-dihydrodibenz[b,e]oxepin-11-one.

The compound so obtained had the following melting point:

Melting point 92°–93° C.

Further, the sequence of reactions in the Reference Example is indicated by the following reaction formulae:

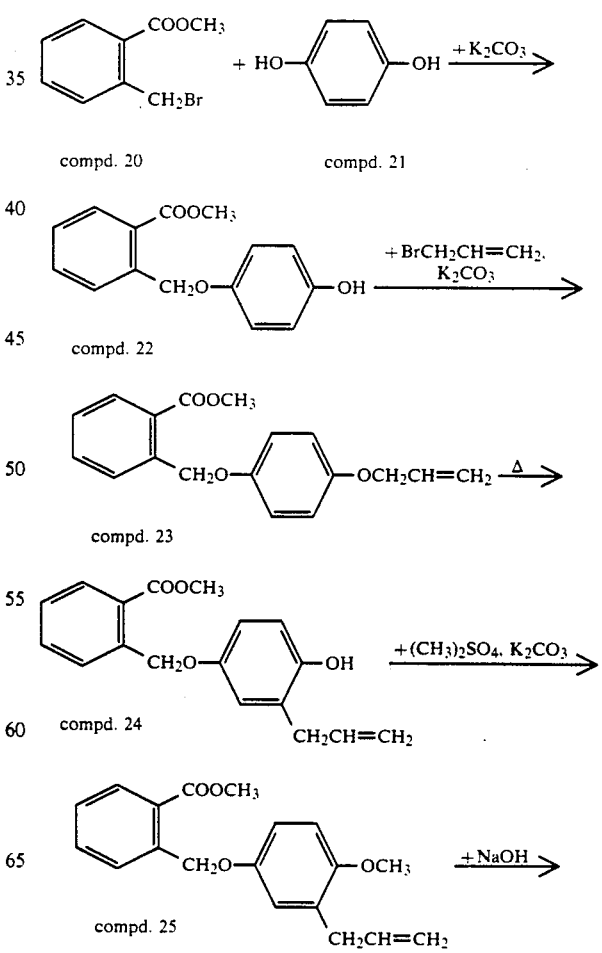

-continued

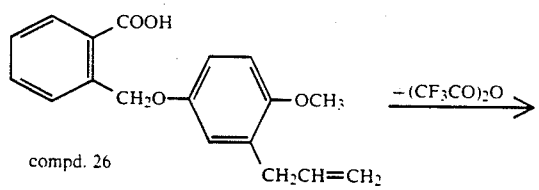

compd. 26

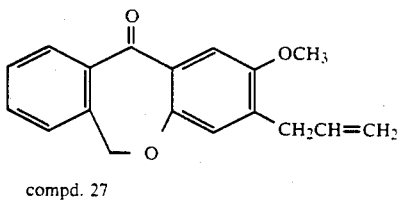

compd. 27

EXAMPLE 1

19.5 grams of 3-allyl-2-methoxy-6,11-dihydrodibenz[-b,e]oxepin-11-one obtained in the above Reference Example were dissolved in a mixed liquid consisting of 400 ml of acetone, 150 ml of acetic acid and 150 ml of water and incorporated in portions with 44 g of potassium permanganate at a temperature of 10°-15 C. over a period of 4 hours, after which the whole was agitated at 15° C. for 1 hour. After the end of the reaction, the unreacted potassium permanganate was decomposed with sodium hydrogen sulfite, after which the insoluble materials in the reaction mixture were filtered out and then the filtrate obtained was evaporated to dryness under a reduced pressure. The residue obtained was incorporated with water to precipitate crystals which were then filtered off. The crystals so filtered off were adsorbed in silica gel packed in a column and developed with a 7:1 chloroform-methanol mixed solution (silica gel column chromatography). The resulting effluent was freed from the solvent by distillation, after which the residue obtained was recrystallized from ethyl acetate thereby to obtain 5.6 g of 2-methoxy-6,11-dihydro-11-oxodibenz[b,e]oxepin-3-acetic acid in the form of colorless needle-like crystals.

The compound so obtained had the following melting point and elemental analysis:

| Melting point | 222–224° C. | |
|---|---|---|
| Elemental analysis | $C_{17}H_{14}O_5$ | |
| Theoretical | C: 68.45% | H: 4.73% |
| Found | C: 68.59% | H: 4.78% |

Further, the reaction formula showing the reaction in Example 1 is as follows:

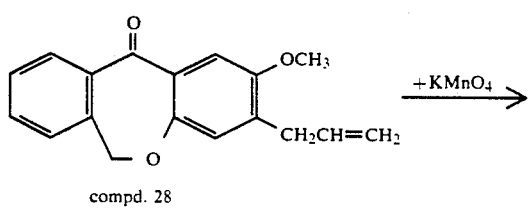

compd. 28

-continued

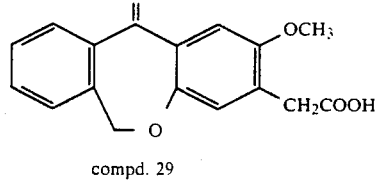

compd. 29

EXAMPLE 2

17.8 grams of 2-(1'-butene-3'-yl)-7-chloro-3-ethoxy-4methyl-6,11-dihydrodibenz[ b,e]oxepin-11-one were dissolved in a mixed liquid consisting of 400 ml of acetone, 150 ml of acetic acid and 150 ml of water and then incorporated in portions with 31.5 g of potassium permanganate at a temperature of 20°-25 C. over a period of 2 hours, after which the whole was agitated at 25° C. for 1 hour. After the end of the reaction, the procedure of Example 1 was followed thereby to obtain 9.5 g of 2-(7-chloro-3-ethoxy-4-methyl-6,11-dihydro-11-oxodibenz[b,e]oxepin-2-yl)propionic acid.

The compound so obtained had the following melting point and elemental analysis:

| Melting point | 192–194° C. | |
|---|---|---|
| Elemental analysis | $C_{20}H_{19}ClO_5$ | |
| Theoretical | C: 64.09% | H: 5.11% |
| Found | C: 64.26% | H: 5.19% |

Further, the reaction formula showing the reaction in Example 2 mentioned above is as follows:

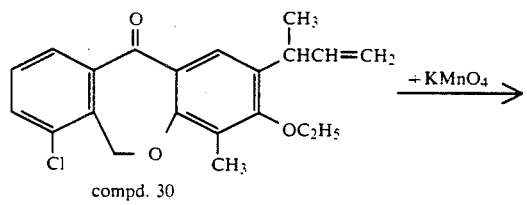

compd. 30

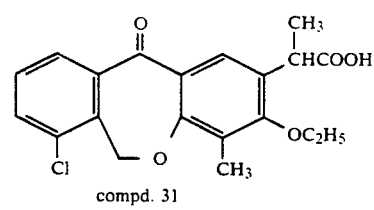

compd. 31

EXAMPLE 3

14.7 grams of 3-(1'-butene-3'-yl)-2-methoxy-6,11-dihydrodibenz[b,e]oxepin-11-one were dissolved in a mixed liquid consisting of 400 ml of acetone, 150 ml of acetic acid and 150 ml of water, incorporated little by little with 31.6 g of potassium permanganate at a temperature of 15°-20 C. over 1 hour and then agitated at 25° C. for 1 hour. After the end of the reaction, the unreacted potassium permanganate was decomposed with sodium hydrogensulfite, after which the insoluble materials in the reaction mixture were filtered out and then the resulting filtrate was freed from the solvent under a reduced pressure. The residue obtained was dissolved in chloroform, washed with water and extracted with a 10% sodium hydroxide aqueous solution, after which the resulting alkaline layer was acidified with 10% hydrochloric acid to precipitate crystals. The crystals so precipitated were filtered off and recrystallized from ethyl acetate thereby to obtain 8.0 g of 2-(2-methoxy-6,11-dihydro-11-oxodibenz[b,e]oxepin-3-yl) propionic acid which was colorless needle-like crystals.

The compound so obtained had the following melting point and elemental analysis:

| Melting point | 160–162° C. | |
|---|---|---|
| Elemental analysis | C₁₈H₁₆O₅ | |
| Theoretical | C: 69.22% | H: 5.16% |
| Found | C: 69.27% | H: 5.21% |

Further, the reaction formula showing the reaction in Example 3 mentioned above is as follows:

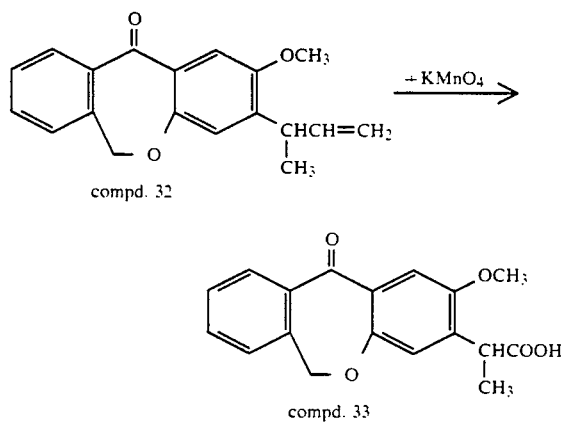

EXAMPLE 4

3.3 grams of 2-(2-ethoxy-6,11-dihydro-11-oxodibenz[b,e]oxepin-3-yl) propionic acid were dissolved in 50 m( of tetrahydrofuran, incorporated with 1.1 g of triethylamine, cooled to −5° C. and then incorporated dropwise with 1.2 g of ethyl chlorocarbonate, after which the whole was agitated for 15 minutes. Next, the reaction mixture obtained was incorporated with 0.85 g of hydroxylamine hydrochloride and 1.5 g of triethylamine and then reacted together at a temperature of 0°–5° C. for 2 hours. After the end of the reaction, the resulting reaction mixture was freed from the solvent to obtain a residue which was incorporated with water to precipitate crystals. The crystals so precipitated were filtered off and recrystallized from ethyl acetate thereby to obtain 3.2 g of 2-(2-ethoxy-6,11-dihydro-11-oxodibenz[b,e]oxepin-3-yl) propionyl hydroxiamic acid which was colorless needle-like crystals.

The compound so obtained had the following melting point and elemental analysis:

| Melting point | 182–183° C. | | |
|---|---|---|---|
| Elemental analysis | C₁₉H₁₉NO₅ | | |
| Theoretical | C: 66.85% | H: 5.61% | N: 4.10% |
| Found | C: 66.73% | H: 5.52% | N: 4.05% |

Further, the reaction formula showing the reaction in Example 4 mentioned above is as follows:

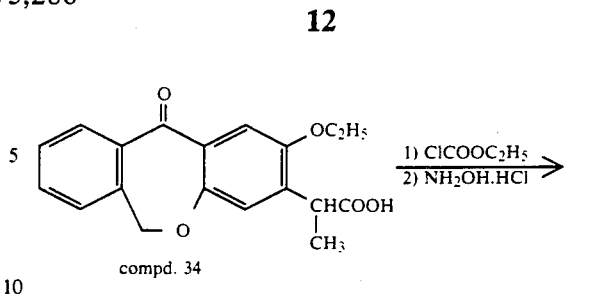

EXAMPLE 5

3.1 grams of 2-(2-methoxy-6,11-dihydro-11oxodibenz[b,e]oxepin-3-yl) propionic acid were dissolved in 40 ml of acetone, incorporated with 1.9 g of ethyl iodide and 0.82 g of potassium carbonate and then reacted together under reflux for 5 hours. After the end of the reaction, the reaction mixture was filtered to remove the insoluble materials therefrom, after which the filtrate obtained was evaporated to dryness under a reduced pressure to obtain a residue. The residue obtained was dissolved in ether, washed with water, dehydrated, freed from the solvent and then distilled under a reduced pressure thereby to obtain 3.0 g of ethyl-2-(2-methoxy-6,11-dihydro-11oxodibenz[b,e]oxepin-3-yl) propionate which was oily.

The above distillation under the reduced pressure was effected using a glass tube oven (Tradename of GTO-250R; rotation type) produced by Shibata Kagaku Kikai Kogyo Co., Ltd., Japan, and the distillation temperature (the boiling point of the resulting compound) was shown by the temperature of the column.

The compound so obtained had the following boiling point and elemental analysis:

| Boiling point | 165–170° C./0.5 mmHg | |
|---|---|---|
| Elemental analysis | C₂₀H₂₀O₅ | |
| Theoretical | C: 70.58% | H: 5.92% |
| Found | C: 70.69% | H: 5.84% |

Further, the reaction formula showing the reaction in Example 5 mentioned above is as follows:

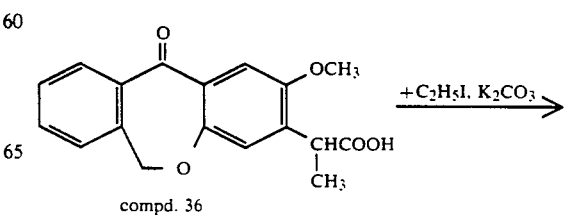

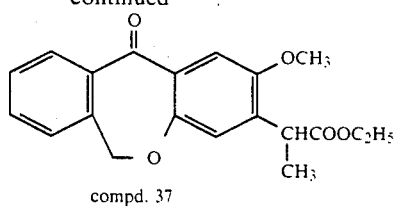

compd. 37

EXAMPLE 6

3.1 grams of 2-(2-methoxy-6,11-dihydro-11ox-odibenz[b,e]oxepin-3-yl) propionic acid were dissolved in 40 ml of benzene, incorporated with 3.6 g of thionyl chloride, refluxed for 5 hours, and then evaporated to dryness under a reduced pressure.

The residue obtained was dissolved in 30 ml of acetone, incorporated dropwise into 30 m( of an aqueous solution containing 2.3 g of glycine and 2.7 g of sodium carbonate and then reacted together at room temperature for 2 hours.

After the end of the reaction, the reaction mixture obtained was incorporated with 50 ml of cooled water, weakly acidified with 5% hydrochloric acid to precipitate crystals which were filtered off and then recrystallized from ethyl acetate thereby to obtain 2.5 g of 2-(2-methoxy-6,11-dihydro-11-oxodibenz[b,e]oxepin-3-yl) propionic acid glycine amide which was light-yellow needle-like crystals.

The compound so obtained had the following melting point and elemental analysis:

| Melting point | 159–161° C. | | |
|---|---|---|---|
| Elemental analysis | $C_{20}H_{19}NO_6$ | | |
| Theoretical | C: 65.03% | H: 5.19% | N: 3.79% |
| Found | C: 65.15% | H: 5.24% | N: 3.88% |

Further, the reaction formula showing the sequence of reactions in Example 6 mentioned above is as follows:

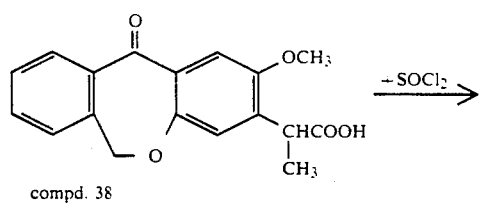

compd. 38

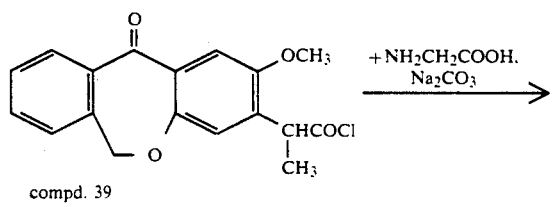

compd. 39

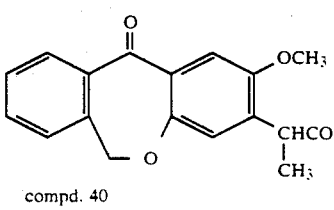

compd. 40

EXAMPLE 7

6.66 grams of thallium trinitrate were dissolved in a mixed liquid of 6 ml of a 60% aqueous solution of perchloric acid and 50 ml of methanol and incorporated with 2.8 g of 2-acetyl-3-methoxy-6,11-dihydrodibenz[b,e]oxepin-11-one, after which the whole was agitated at room temperature for 1 hour and further agitated under reflux for additional 4 hours.

After the end of the reaction, the reaction mixture incorporated with 200 ml of cooled water and extracted with 150 ml of chloroform, after which the resulting organic layer was washed with water, dehydrated and evaporated to dryness under a reduced pressure. The residue obtained was adsorbed in a column packed with silica gel and developed with a 2:1 hexane.ethyl acetate mixed solution (silica gel column chromatography). The resulting effluent was freed from the solvent to obtain a residue which was recrystallized from ethyl acetate thereby to obtain 2.0 g of methyl-3-methoxy-6,11-dihydro-11-oxodibenz[b,e]oxepin-2-acetate acetate which was colorless needle-like crystals.

The compound so obtained had the following melting point and elemental analysis:

| Melting point | 112–114° C. | |
|---|---|---|
| Elemental analysis | $C_{18}H_{16}O_5$ | |
| Theoretical | C: 69.22% | H: 5.16% |
| Found | C: 69.12% | H: 5.27% |

Further, the reaction formula showing the reaction in Example 7 mentioned above is as follows:

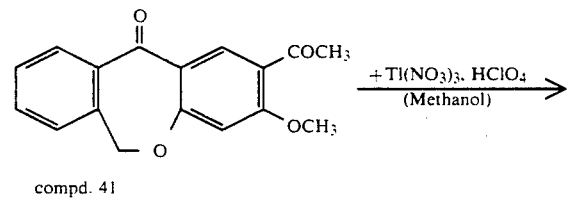

compd. 41

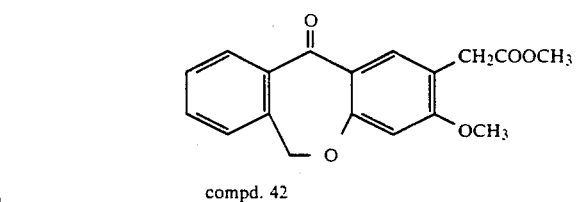

compd. 42

EXAMPLE 8

A mixture of 2.0 g of methyl-3-methoxy-6,11-dihydro-11-oxodibenz[b,e]oxepin-2-acetate and 100 ml of 5% hydrochloric acid was agitated under reflux for 16 hours.

After the reaction mixture had been cooled, the crystals precipitated were filtered off, washed with water and then recrystallized from tetrahydrofuran thereby to obtain 1.53 g of 3-methoxy-6,11-dihydro-11-oxodibenz[b,e]oxepin-2-acetic acid which was colorless needle-like crystals.

The compound so obtained had the following melting point and elemental analysis:

| Melting point | 243–245° C. |
|---|---|
| Elemental analysis | $C_{17}H_{14}O_5$ |

| -continued | | |
|---|---|---|
| Theoretical | C: 68.45% | H: 4.73% |
| Found | C: 68.27% | H: 4.78% |

Further, the reaction formula showing the reaction in Example 8 mentioned above is as follows:

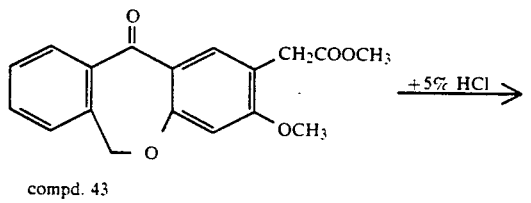
compd. 43

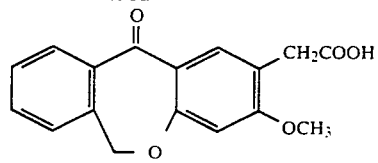
compd. 44

EXAMPLES 9-45

In accordance with the procedures of Examples 1-8, there were prepared the compounds of the present invention indicated in the following Table 1. The melting or boiling points of the thus prepared compounds are indicated in Table 1.

TABLE 1

| Example No. | $R^1$ | $R^2$ | $R^3$ | $R^4$ | Melting point [°C.] (*1) or Boiling point [°C.] (*2) |
|---|---|---|---|---|---|
| 9 | H | H | —OC$_2$H$_5$ | —CH(CH$_3$)COOH | 154–156 (*1) |
| 10 | H | H | —OC$_2$H$_5$ | —CH$_2$COOH | 187–189 (*1) |
| 11 | 7-F | H | —OCH$_3$ | —CH(CH$_3$)COOH | 162–164 (*1) |
| 12 | 7-Cl | H | —OCH$_3$ | —CH(CH$_3$)COOH | 176–178 (*1) |
| 13 | 7-Cl | H | —OCH$_3$ | —CH$_2$COOH | 189–191 (*1) |
| 14 | 7-CH$_3$ | H | —OCH$_3$ | —CH(CH$_3$)COOH | 166–168 (*1) |
| 15 | 7-OCH$_3$ | H | —OCH$_3$ | —CH(CH$_3$)COOH | 101–104 (*1) |
| 16 | 8-F | H | —OCH$_3$ | —CH(CH$_3$)COOH | 210–212 (*1) |
| 17 | 8-Br | H | —OCH$_3$ | —CH(CH$_3$)COOH | 225–227 (*1) |
| 18 | 8-Br | H | —OCH$_3$ | —CH$_2$COOH | 230–233 (*1) |
| 19 | 8-CH$_3$ | H | —OCH$_3$ | —CH(CH$_3$)COOH | 193–195 (*1) |
| 20 | 9-F | H | —OCH$_3$ | —CH(CH$_3$)COOH | 159–161 (*1) |
| 21 | 9-F | H | —OCH$_3$ | —CH$_2$COOH | 240–242 (*1) |
| 22 | 9-Cl | H | —OCH$_3$ | —CH(CH$_3$)COOH | 200–202 (*1) |
| 23 | 9-Cl | H | —OC$_2$H$_5$ | —CH(CH$_3$)COOH | 173–175 (*1) |

TABLE 1-continued

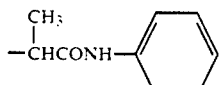

| Example No. | $R^1$ | $R^2$ | $R^3$ | $R^4$ | Melting point [°C.] (*1) or Boiling point [°C.] (*2) |
|---|---|---|---|---|---|
| 24 | 9-$CH_3$ | H | —$OCH_3$ | —$CH_2COOH$ | 228~230 (*1) |
| 25 | 9-$CH_3$ | H | —$OCH_3$ | —CH($CH_3$)COOH | 146~148 (*1) |
| 26 | H | $CH_3$ | —$CH_2COOH$ | —$OCH_3$ | 184~186 (*1) |
| 27 | 7-Cl | $CH_3$ | —$CH_2COOH$ | —$OCH_3$ | 211~213 (*1) |
| 28 | 7-Cl | $CH_3$ | —$CH_2COOH$ | —$OC_2H_5$ | 188~191 (*1) |
| 29 | 7-Cl | $CH_3$ | —CH($CH_3$)COOH | —$OCH_3$ | 187~190 (*1) |
| 30 | 8-Br | $CH_3$ | —$CH_2COOH$ | —$OCH_3$ | 254~256 (*1) |
| 31 | 8-Br | $CH_3$ | —CH($CH_3$)COOH | —$OCH_3$ | 213~215 (*1) |
| 32 | 9-Cl | $CH_3$ | —CH($CH_3$)COOH | —$OCH_3$ | 197~200 (*1) |
| 33 | 9-$CH_3$ | $CH_3$ | —$CH_2COOH$ | —$OCH_3$ | 179~181 (*1) |
| 34 | 9-$CH_3$ | $CH_3$ | —CH($CH_3$)COOH | —$OCH_3$ | 194~195 (*1) |
| 35 | H | H | —$OCH_3$ | —CH($CH_3$)$CONH_2$ | 199~203 (*1) |
| 36 | H | H | —$OCH_3$ | 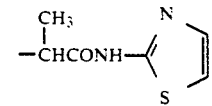 | 178~182 (*1) |
| 37 | H | H | —$OCH_3$ | 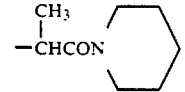 | 211~214 (*1) |
| 38 | H | H | —$OCH_3$ | 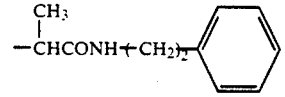 | 160~162 (*1) |
| 39 | H | H | —$OCH_3$ | 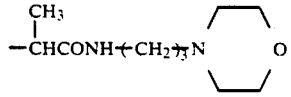 | 134~137 (*1) |
| 40 | H | H | —$OCH_3$ | —CH($CH_3$)CONH($CH_2$)$_3$N(morpholine) | 117~120 (*1) |
| 41 | H | H | —$OCH_3$ | 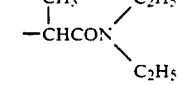 | 180~185/ 0.5 mmHg (*2) |

TABLE 1-continued

Structure: dibenzoxepinone with substituents $R^1$, $R^2$, $R^3$, $R^4$

| Example No. | $R^1$ | $R^2$ | $R^3$ | $R^4$ | Melting point [°C] (*1) or Boiling point [°C] (*2) |
|---|---|---|---|---|---|
| 42 | H | H | —OCH$_3$ | —CHCOO(CH$_2$)$_{15}$CH$_3$ with CH$_3$ branch | 165~170/ 0.1 mmHg (*2) |
| 43 | H | H | —OCH$_3$ | —CHCOOCH$_2$OC$_2$H$_5$ with CH$_3$ branch | 175~180/ 0.1 mmHg (*2) |
| 44 | H | H | —OCH$_3$ | —CHCOO(CH$_2$)$_{15}$N(morpholino) with CH$_3$ branch | 122~127 (*1) |
| 45 | H | H | —OCH$_3$ | —CHCOOCH$_2$COOC$_2$H$_5$ with CH$_3$ branch | 175~180/ 0.1 mmHg (*2) |

ACTIONS

In order to substantiate the medicinal efficacy and safety of the compounds of the present invention, methods for the pharmacological experiment of said compounds and the pharmacological data obtained by the experiment, were carried out as indicated hereunder.

PHARMACOLOGICAL EXPERIMENT 1

CARRAGEENIN-INDUCED PAW EDEMA EXPERIMENT IN RATS

As test animals, there were provided groups each consisting of 7 male rats of Wistar strain each weighing approximately 150 g. Each of the compounds of the present invention indicated in the following Table 2 was orally administered to the rats of one group at the dose indicated in the same Table. Sixty minutes later, 0.1 ml of 1%—carrageenin was subcutaneously injected into the paw of each of the rats to induce the reaction. For comparison, a comparative compound as shown in Table 2 was also used in the same manner as above. Since then, the volume of paw edema of each of the rats was measured with the lapse of time. The efficacies of the compounds of the present invention and the comparative compound are respectively expressed in terms of inhibition rates (average value in each group) in the orally administered groups, which were obtained 3 hours after the induction of the reaction, in comparison with the inhibition ratio in the control group to which none of the medicinal compounds was orally administered. The results are shown in the following Table 2.

TABLE 2

| Compound tested | Dose (mg/kg) | Inhibition (%) |
|---|---|---|
| Compound of Example 1 | 3 | 38.3 |
| Compound of Example 3 | 3 | 41.5 |
| Compound of Example 12 | 3 | 31.1 |
| Compound of Example 17 | 3 | 32.5 |
| Compound of Example 19 | 3 | 37.6 |
| Comparative Compound 1 (*1) | 3 | 14.0 |

(*1): 2-(6,11-dihydro-11-oxodibenz[b,e]oxepin-3-yl)propionic acid

PHARMACOLOGICAL EXPERIMENT 2

ADJUVANT ARTHRITIS EXPERIMENT IN RATS 0.6 mg/0.1 ml of Mycobacterium butyricum suspended in liquid paraffin were subcutaneously administered to the root of the tail of each of male rats of Wistar strain each weighing approximately 240 g. Among the above administered rats, the rats which definitely caused arthritis at the hind paws thereof 17 days later than the subcutaneous administration were selected for use as test animals. The compound of the present invention (the compound of Example 3) was orally administered once a day for 7 days to each of the selected rats at the dose indicated in the following Table 3. The inhibitory effect on the adjuvant arthritis was investigated referring, as a guide to the investigation, to the inhibition effect on swelling of the hind paws of each of the rats. In each of the tested rats, the inhibition rate was calculated by comparing the swelling volume ratio of the tested rat determined by the following formula with that of the rat as the control (to which none of the compounds was orally administered) and is shown in the following Table 3.

Swelling volume ratio = {(paw volume measured 24 days after the subcutaneous administration)-(original paw volume of normal rat)}/ {(paw volume measured 17 days after the subcutaneous administration)-(original paw volume of normal rat)} × 100

TABLE 3

| Compound tested | Dose (mg/kg) | Inhibition (%) |
|---|---|---|
| Compound of Example 3 | 0.1 | 10.6 |
| Compound of Example 3 | 0.3 | 28.3 |
| Compound of Example 3 | 1.0 | 43.8 |
| Compound of Example 3 | 3.0 | 66.0 |
| Compound of Example 3 | 10.0 | 70.0 |
| Compound of Example 3 | 30.0 | 65.6 |

PHARMACOLOGICAL EXPERIMENT 3

GASTRIC MUCOUS TROUBLE EXPERIMENT IN RATS

As test animals, there were provided groups each consisting of 7 male rats of Wistar strain each weighing approximately 160 g. Each of the compounds indicated in the following Table 4 was orally administered to the rats of one group at the dose indicated in the same Table after their fasting for 18 hours. 3.5 hours later, the rats so administered were dissected to remove therefrom the stomachs into which 10 ml of 70% ethanol were injected to fix them. The stomachs so fixed were cut, washed with water and then visually observed to find whether ulcers were formed therein. The results obtained are shown in the following Table 4.

TABLE 4

| Compound tested | Dose (mg/kg) | Ulcer formation (incidence) |
|---|---|---|
| Compound of Example 1 | 100 | 0/7 |
| Compound of Example 3 | 100 | 0/7 |
| Compound of Example 12 | 100 | 0/7 |
| Compound of Example 17 | 100 | 0/7 |
| Compound of Example 19 | 100 | 0/7 |
| Compound of Example 30 | 100 | 0/7 |
| Comparative compound 1 (*1) | 100 | 5/7 |
| Comparative compound 2 (*2) | 10 | 7/7 |

(*1): The same compound as said comparative compound 1.
(*2): Indomethacin.

INDUSTRIAL APPLICABILITY

As is clear from the foregoing carrageenin-induced paw edema experiment of Pharmacological Experiment 1, the compounds of the present invention have excellent medicinal efficacies or inhibiting actions on carrageenin-induced paw edema which are about at least twice as strong as those of 2-(6,11 dihydro-11-oxodibenz[b,e]oxepin-3-yl)propionic acid (comparative compound 1: described in said Japanese Pat. Appln. Laid-Open Gazette No. 50-35179 and "Journal of Medicinal Chem., Vol. 19, No. 7, pp. 941-946 (1976)") of which chemical structure is similar to those of the compounds of the present invention.

Further, as is clear from the foregoing adjuvant arthritis experiment of Pharmacological Experiment 2, the compounds of the present invention have conspicuous inhibiting actions on adjuvant arthritis even if the dose of the compounds is small.

Furthermore, as is clear from the foregoing gastric mucous trouble experiment of Pharmacological Experiment 3, the compounds of the present invention will not cause gastric mucous membrane disturbances at all when administered at a dose of 100 mg/kg. In contrast, said comparative compound 1 and indomethacin will frequently cause such disturbances when administered at doses of 100 mg/kg and 10 mg/kg, respectively.

As has been so far described, the compounds of the present invention are useful as very excellent antiphlogistics and will exhibit conspicuous pharmacological actions with high safety and substantially without side effects on gastric mucous membrane when administered, whereas conventional non-steroid type antiphlogistics will particularly exhibit such side effects when administered.

Accordingly, the compounds of the present invention are very industrially useful as non-steroid type antiphlogistics having excellent medicinal efficacy and high safety.

We claim:

1. A compound which is a dibenz[b,e]oxepin derivative of formula (I)

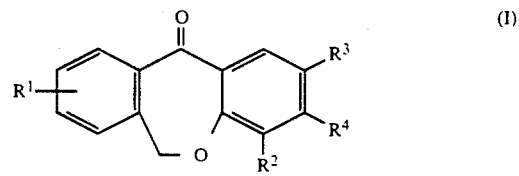

wherein $R^1$ and $R^2$ are each a hydrogen atom, halogen atom, lower alkyl group of lower akoxy group; one of $R^3$ and $R^4$ is a lower alkoxy group, and the other is a group of formula (11)

wherein $R^5$ is a hydrogen atom or lower alkyl group, A is a hydroxyl group, $-O(CH_2)_m-R^6$ wherein m is an integer of 1-6, $R^6$ is a hydrogen atom, lower akyl group, lowr alkoxy group, piperazino group, morpholino group, piperidino group, pyrrolidino group or lower alkoxycarbonyl group, di-lower alkylamino group or $-NH(CH_2)_n-R^7$ wherein n is an integer of 0-3, $R^7$ is a hydrogen atom, hydroxyl group, phenyl group, thiazole group, piperazino group, morpholino group, piperidino group or pyrrolidino group.

2. The compound according to claim 1 which is 2-methoxy-6,11-dihydro-11-oxodibenz[b,e]oxepin-3-acetic acid.

3. The compound according to claim 1 which is 2-methoxy-6,1-dihydro-11-oxodibenz[b,e]oxepin-3-yl propionic acid.

4. The compound according to claim 1 wherein $R^1$ is chlorine in the 7-position, $R_2$ is H, $R_3$ is methoxy, $R_4$ is

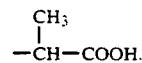

5. The compound according to claim 1 wherein $R^1$ is bromine in the 8-position, $R^2$ is H, $R_3$ is methoxy, $R_4$ is

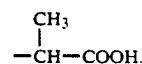

6. The compound according to claim 1 wherein $R^1$ is methyl in the 8-position, $R^2$ is H, $R^3$ is methoxy, $R^4$ is 7. The compound according to claim 1 wherein $R^1$ is bromine in the 8-position, $R^2$ is methyl $R^3$ is $-CH_2-COOH$, $R^4$ is methoxy.

8. An antiphlogistic agent comprising a compound which is a dibenz[b,e]oxepin derivative of formula (1)

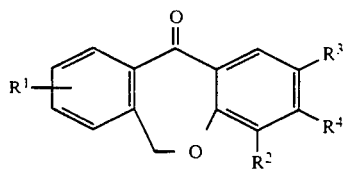

wherein $R^{11}$ and $R^2$ are each a hydrogen atom, halogen atom, lower alkyl group or lower alkoxy group, one of $R^3$ and $R^4$ is a lower akoxy group, and the other is a group of formula (II)

wherein $R^5$ is a hydrogen atom or lower alkyl group, A is an hydroxyl group, $-O(CH_2)_m-R^6$ wherein m is an integer of 1-6, $R^6$ is a hydrogen atom, lower alkyl group, lower alkoxy group, piperazino group, morpholino group, piperidino group, pyrrolidino group or lower alkoxycarbonyl group, di-lower alkylamino group or $-NH(CH_2)_n-R^7$ wherein n is an integer of 0-3, $R^7$ is a hydrogen atom, hydroxyl group, phenyl group, thiazole group, piperazino group, morpholino group, piperidino group or pyrrolidino group.

* * * * *

UNITED STATES PATENT AND TRADEMARK OFFICE
CERTIFICATE OF CORRECTION

PATENT NO. : 5,175,286
DATED : December 29, 1992
INVENTOR(S) : Saita, et al

It is certified that error appears in the above-indentified patent and that said Letters Patent is hereby corrected as shown below:

On the title page: Item [30] Foreign Application
    Priority Data 63-236780

Signed and Sealed this

Twenty-sixth Day of October, 1993

Attest:

BRUCE LEHMAN

Attesting Officer         Commissioner of Patents and Trademarks